United States Patent [19]
Matsuhashi et al.

[11] Patent Number: 5,955,334
[45] Date of Patent: Sep. 21, 1999

[54] PROCESS FOR CULTURING MICROORGANISMS OR CELLS USING SOUND WAVES

[75] Inventors: Michio Matsuhashi, Tokyo; Sugio Otani, Gunma; Tomohiko Kaneko, Shizuoka, all of Japan

[73] Assignee: Research Development Corporation of Japan, Japan

[21] Appl. No.: 08/688,923

[22] Filed: Jul. 31, 1996

[30] Foreign Application Priority Data

Jan. 5, 1996 [JP] Japan ............................................ 8-372

[51] Int. Cl.$^6$ .................................................. C12N 13/00
[52] U.S. Cl. ...................................... 435/173.8; 435/173.1
[58] Field of Search ............................... 435/173.1, 173.8

[56] References Cited

U.S. PATENT DOCUMENTS

| | | | |
|---|---|---|---|
| 3,847,803 | 11/1974 | Fisk | 210/605 |
| 4,053,394 | 10/1977 | Fisk | 210/605 |

FOREIGN PATENT DOCUMENTS 08275771 10/1996 Japan .

OTHER PUBLICATIONS

Matsuhashi et al. (Spr., 1996) Microb. Drug Resist., 2(1), "Cellular Signals Regulating Antibiotic Sensitivities in Bacteria", pp. 91–93.

Sevast'yanova (1979) Vestn Akad Med Nauk SSSR, 2, "Characteristics of the Biological Effect of Millimeter Range Radio Waves and Possibilities of Their Use in Medicine", pp. 65–68.

Matsuhashi et al. (1995) J. Bacteriol., 177(3), "Studies on Carbon Material Requirements for Bacterial Proliferation and Spore Germination under Stress Conditions: a New Mechanism Involving Transmission of Physical Signals", pp. 688–693.

Matsuhashi et al. (1996) J. Gen. Appl. Microbiol., 42(4), "*Bacillus caboniphilus* Respond to Growth–Promoting Physical Signals from Cells of Homologous and Heterologous Bacteria", pp. 315–323.

Norris et al. (1997) Molecular Microbiology, 24(4), "Micro-Correspondence", pp. 879–880.

Fujita et al. (Jan. 1996) Int. J. Syst Bacteriol., 46(1), "Description of *Bacillus–carboniphilus sp–nov*", pp. 116–118.

Michio Matsuhashi et al., Signals Propagating through Air Functioning in Promoting the Reproduction of Plant Cells Plant Cells emit and receive signals transmitted through air I Japan Society for Bioscience, Biotechnology and Agrochemistry, Aug. 1, 1995, Conference Abstracts.

Y. Mano et al., Aerial–Conducting Signals Which Promotes Reproduction of Plant Cells II Japan Society for Bioscience, Biotechnology and Agrochemistry, Aug. 1, 1995, Conference Abstracts.

A.N. Pankrushina et al., Impedance to Generation of Fish Eggs with Aerial–Conducting Signals Emitted by cells Japan Society for Bioscience, Biotechnology and Agrochemistry, Aug. 1, 1995, Conference Abstracts.

Michio Matsuhashi et al., Mechanism of Promotion of Cell propagation by Carbon Compounds Japan Society for Bioscience, Biotechnology and Agrochemistry, Aug. 1, 1995, Conference Abstracts.

K. Endoh et al., Studies on Signals Propagating through Air Using *Bacillus carbonphilus* with a Great Demand for Carbon Compounds under Stress Japan Society for Bioscience, Biotechnology and Agrochemistry, Aug, 1, 1995, Conference Abstracts.

S. Endoh et al., Study on Signal Transduction through Air Using *E. coli, Bacillus carbophilus*, and *Micrococcus luteus* Japan Society for Bioscience, Biotechnology and Agrochemistry, Aug. 1, 1995, Conference Abstracts.

Michio Matsuhashi et al., Possibilities of Involvement of Porous Structures such as Cell Walls in the Transmission of Growth–Regulating Signals Emitted by Cells Japan Society for Bioscience, Biotechnology and Agrochemistry, Aug. 1, 1995, Conference Abstracts.

M. Tobi et al., Studies on Aerial–conducting Signals Using Yeast and Plant buds Seeds Japan Society for Bioscience, Biotechnology and Agrochemistry, Aug. 1, 1995, Conference Abstracts.

M. Yoshimura et al., "Sound wave"signals, emitted by bacteria and yeast cells, regulate the propagation of yeast under alchol stress Japan Society for Bioscience, Biotechnology and Agrochemistry, Aug. 1, 1995, Conference Abstracts.

Michio Matsuhashi et al., Intercellular Signals Propagated through Air Functioning in Regulating the Growth of Cell Communities Society for Pharmentation and Bioengineering, Japan, Oct. 13, 1995, Conference Abstracts.

*Primary Examiner*—Jon P. Weber
*Attorney, Agent, or Firm*—Wenderoth, Lind & Ponack, L.L.P.

[57] ABSTRACT

A process is disclosed for culturing microorganisms or cells isolated from a multicellular organism while exposing the microorganism or cells to sound waves of 5 to 100 kHz. This procedure effects the proliferation and the expression of functions of the cells so exposed. An apparatus for culturing the cells according to this process is also disclosed.

2 Claims, 12 Drawing Sheets

E.coli K12, Antibiotic Medium 3+7%KCl, 42°C 1.5%Agar 1.5%Agar
+2.5%Graphite

Saline

PROCESS FOR CULTURING MICROORGANISMS OR CELLS USING SOUND WAVES

FIELD OF THE INVENTION

This invention relates generally to an apparatus and process for cell culture, and more particularly to a process for culturing a microorganism or cells isolated from a multicellular organism while controlling the proliferation and function expression thereof, and an apparatus for reducing the process to practice.

PRIOR ART

Cell culture has been extensively applied from technology in various fields of study and for industrial production. Such efforts are designed to grow under artificial nutrient conditions, microorganisms such as bacteria, virus and yeast, or cells isolated from multicellular organisms, including animals and plants (in some cases, hereafter referred to collectively as "cells"), and to grow them over an extended period of time for gene manipulation.

Cell culture processes are available in two types One process is concerned with the cultivation of bacteria, yeast and other microorganisms, a process which provides the basis for genetic recombination and biotechnology, and is also indispensable for the production of useful substances, including antibiotics and yeast.

Another is tissue culture, which deals with animal cells. With a view to closely examining in vitro the functions of a living organ and/or tissue to which the target cell belongs, the technology has been widely applied in comprehensive fields of study on life phenomena, which cover biology, medicine, pharmacology, and agricultural science. It is also employed as a vital industrial production technology which makes use of the functions expressed by a cell or a fused cell to provide interferons, human growth hormone, monoclonal antibodies, and other physiologically active substances. In particular, the culture of animal (human) cells has gained increasing importance because for gene therapy, it is vital to secure recombinant cells with foreign genes. During recent years, much attention has been rivetted on the importance of plant cell culture in the improvement of crops using protoplasts, callus culture, or fused cells and also in the mass-production technology of useful alkaloid.

It is exceedingly stressful, however, for cells to be placed in artificial culture conditions, entirely different from the environment where they should live. Although various media have been devised according to the type of cells and the application for which cultured cells are intended, it is not necessarily an easy matter to allow individual cells to actively proliferate under these artificial culture conditions and to effectively express the functions they have. As a result, the conventional process for cell culture has fallen short of producing satisfactory results in the production of useful substances, plant breeding or the preparation of recombinant cells.

SUMMARY OF THE INVENTION

The object of this invention is to provide a novel process for cell culture capable of effectively controlling the proliferation of various cells and the expression of functions thereof under artificial stressful conditions, and an apparatus for reducing the process to practice.

The present invention provides a novel cell culture process comprising one of the following steps of:

(1) culturing cells while exposing them to a sound wave of 5 KHz to 100 kHz;

(2) culturing cells in the presence of a carbon material, a synthetic organic polymer or an inorganic substance;

(3) culturing cells in the presence of a carbon material, a synthetic organic polymer or an inorganic substance while exposing them to a sound wave of 5 KHz to 100 kHz; and (4) culturing cells together with other cells which are separated from the target cells with a carbon material, a synthetic organic polymer or an inorganic substance.

Also provided in accordance with the present invention is an apparatus for culturing cells, comprising:

(5) a culture container for the cells, and a sound wave device designed to transmit a sound wave of 5 kHz to 100 kHz into the culture container;

(6) a culture container for the cells and a means for accomodating a carbon material, a synthetic organic polymer or an inorganic substance; or (7) a culture container for the cells, a sound wave device designed to transmit a sound wave of 5 kHz to 100 kHz into the container, and a means for accomodating a carbon material, a synthetic organic polymer or an inorganic substance within the container.

Accordingly, in accordance with the present invention there has been provided a novel cell culture process capable of effectively controlling the proliferation of various cells and the expression of functions thereof under artificial stress conditions, and an apparatus for implementing the process.

The process and apparatus of this invention provide a number of new possibilities in the field of:

(a) improvement in productivity of useful products through the culture of microorganism cells or cells derived from plants and animals:

(b) improvement of plant breeding by means of gene recombination or cell fusion of plant cells;

(c) securement of necessary amounts of animal recombinant cells for treatment of infectitious diseases and/or gene diseases; and (d) improvement of animals by accelerated proliferation of embryonic stem cells.

DETAILED DESCRIPTION OF THE INVENTION

Figure 1:
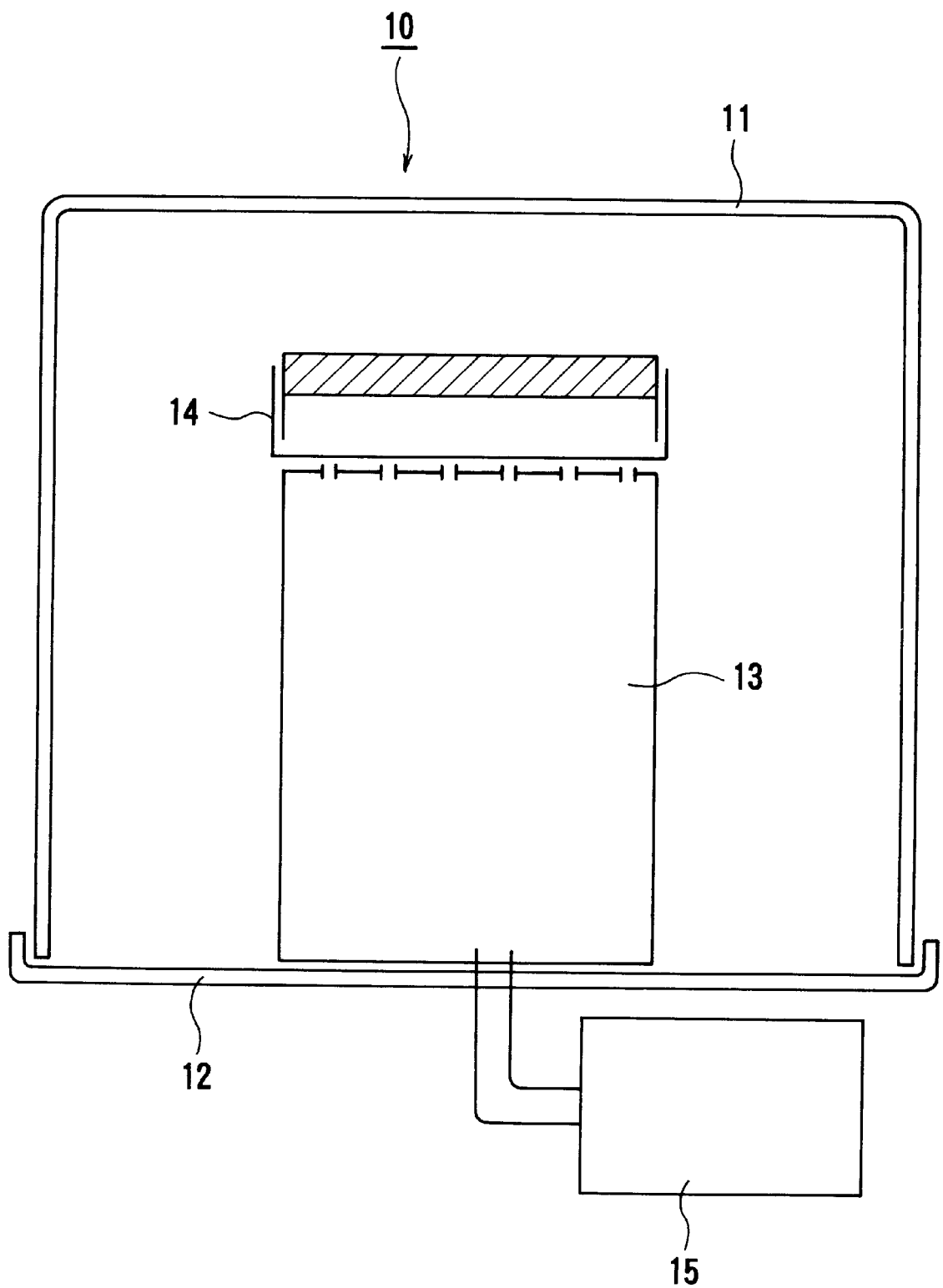
FIG. 1 is a block diagram showing a cell culture apparatus in accordance with the present invention.

The cells cultured by the foregoing process and apparatus of this invention include those of bacteria, virus, yeast and other microorganisms, and/or those isolated from multicellular organisms such as plants and animals. The animal cells include the normal cells, cancer cells or the cell lines, embryonic stem cells and germ cells thereof which are derived from the organs and tissue of individual plants and animals, cells infected with virus or other microorganisms, fused cells, and recombinant cells into which foreign genes are introduced. The plant cells include explant cells, the protoplast and callus thereof. According to this invention, other types of plants cells, such as those infected with microorganisms, fused cells and recombinant cells can also be subjected. This means that the cells to be cultured with the process and apparatus of this invention are to be applied in all fields of study and industrial applications which are users of the cell culture technologies heretofore or hereinafter available.

The sound waves applied to the cells range from 5 to 100 kHz, which represents the range of sound waves naturally discharged by cells. They can be produced by commercially available sound wave producing devices with a loud speaker connected thereto, which have been used from medical purposes or for purpose of accelerating the maturity of food (fruit, etc.), for instance. In those cases of medical use or for maturing food, the sound waves are intended to disrupt cells or to keep particles of a substance in suspension, due to their strong breakage effect. In accordance with this invention, on the other hand, the sound waves used are very weak, produced with 1 to 50 volts. The sound wave producing device used in this invention is capable of arbitrarily varying the type and intensity of the waves to be sent, thereby accelerating, slowing down or even stopping the proliferation of cells and the expression of functions thereof.

The carbon material, synthetic organic polymer or inorganic substance is, for example, graphite, activated carbon, charcoal, cork, timber, plant pith and other carbon materials, foamed polyurethane, foamed polyethylene and other synthetic organic polymers, and soil, sea sand, pumice and other inorganic substances. They can control the proliferation of culture cells and the expression of functions thereof. These substances can, for instance, be used in an echo box.

Very weak sound waves of 5 to 100 kHz, produced by a sound wave producing device or other cells which are being cultured together with the target cells, may strike against to the carbon material, synthetic organic polymer or inorganic substance so that they are reflected therefrom, and the echoed sound wave is exposed to the targeted cells. Furthermore, as these weak sound waves are signals transmitted by cells themselves, two kinds of cells are cultured in the same space which is divided with a synthetic organic polymer or an inorganic substance, thereby causing one cell to transmit sound waves to the other.

EXAMPLES

The following non-limited examples serve to illustrate the preferred process and apparatus according to this invention.

EXAMPLE 1

A cell culture apparatus as indicated in FIG. 1 was fabricated to evaluate how cells would proliferate therein.

The cell culture apparatus (10) consisted of a polypropyrene cylindrical container (11) which had a dimension of 100 mmh×150 mmφ×2 mm and stood inverted with a polyethylene cover (12) thereof at the bottom. On the cover (12) there was mounted a loudspeaker (13), on which a plastic Petri dish (14) was placed.

A function generator (15) was connected to said loudspeaker (13).

(A) Procedure:

With a medium placed into the plastic Petri dish (14) of the apparatus (10), bacteria (*Bacillus carboniphilus, Bacillus subtilis, Escherichia coli* and *Micrococcus luteus*) and yeast (*Saccharomyces cerevisiae*) were cultured for 2 to 10 days in an incubators while sound waves were produced from the loud speaker (13), and the number of colonies was counted. The number of all bacteria was measured with a photoelectric photometer.

The cells, media and culture temperature used are shown in Table 1.

TABLE 1

| Species | Strain | Medium | Temp. |
| --- | --- | --- | --- |
| B. carboniphilus | Kasumi No.6 (JCM 9731) | AM3/2: 1% KCl: 1.5% Agar | 44° C. |
| B.subtilis |  | AM3 : 16% KCl: 1.5% Agar | 44° C. |
| E.coli | K-12 | AM3 : 7% KCl: 1.5% Agar | 42° C. |
| M.luteus | JAM 1056 | AM3 : 7% KCl: 1.5% Agar | 33° C. |
| S.cerevisiae | Kyokai No.7 | AM3 : 7% KCl: 1.5% Agar | 33° C. |

Notes
AM3 : Bacto Antibiotic Medium 3
AM3/2: AM3 solution diluted to two times with water (B) Results:

Accelerated proliferation of *Bacillus carboniphilus, Bacillus subtilis* and *Escherichia coli* when they were cultured in this culture apparatus (10) is indicated in Table 2. Table 2 clearly indicates that these bacteria substantially increased the number of colonies that grew in the presence of sound waves of 5 to 100 kHz, produced with 10 volts and 20 volts.

TABLE 2

| Species | Inoculated number | Frequency (kHz) | Voltage (V) | Number of colonies |
| --- | --- | --- | --- | --- |
| B. carboniphilus | 13,000 | 10 | 10 | 2,492 |
|  | 13,000 | — | — | 0 |
|  | 7,000 | 10 | 10 | 202 |
|  | 7,000 | — | — | 0 |
| B.subtilis | 10,000 | 10 | 20 | 1,188 |
|  | 10,000 | — | — | 388 |
|  | 10,000 | 20 | 20 | 8,053 |
|  | 10,000 | — | — | 1,627 |
| E.coli | 19,000 | 10 | 10 | 472 |
|  | 19,000 | — | — | 6 |

As shown in Table 3, it was also confirmed that the viable count of *Micrococcus luteus* was significantly increased in the presence of sound waves.

TABLE 3

| Species | Frequency (kHz) | Voltage (V) | Viable count (ODU) |
|---|---|---|---|
| M.luteus | 5 | 20 | 31.0 |
|  | — | — | 17.0 |
|  | 10 | 10 | 39.0 |
|  | — | — | 0.0 |
|  | 20 | 10 | 7.9 |
|  | — | — | 0.95 |
|  | 30 | 5 | 0.75 |
|  | — | — | 0.1 |
|  | 60 | 5 | 6.25 |
|  | — | — | 2.5 |

On top of the foregoing findings, it was observed that exposure of sound waves to target cells repressed the proliferation thereof. The number of colonies of *Bacillus subtilis* formed (Table 4) and the viable count of *Micrococcus luteus* (Table 5) were decreased substantially in the presence of sound waves. It was observed that similar sonic effects upon acceleration and slowing down of proliferation occurred with regard to yeast (Table 6 indicates acceleration effects and Table 7 repressing effects).

The following tendencies were observed with acceleration and slowing down of cell proliferation as a result of the exposure of sound waves: sound waves with low frequency, produced with low voltages, accelerate cell proliferation, while the sound waves with relatively high frequency, produced with higher voltages, slow it down.

TABLE 4

| Species | Inoculated number | Frequency (kHz) | Voltage (V) | Number of colonies |
|---|---|---|---|---|
| B.subtilis | 10,000 | 100 | 20 | 214 |
|  | 10,000 | — | — | 482 |

TABLE 5

| Species | Frequency (kHz) | Voltage (V) | Viable count (ODU) |
|---|---|---|---|
| M.luteus | 5 | 20 | 0.1 |
|  | — | — | 2.0 |
|  | 10 | 20 | 0.1 |
|  | — | — | 2.0 |
|  | 20 | 20 | 0.3 |
|  | — | — | 4.5 |

TABLE 6

| Species | Inoculated number | Frequency (kHz) | Voltage (V) | Number of colonies |
|---|---|---|---|---|
| S.cerevisiae | 4,500 | 10 | 2 | 172 |
|  | 4,500 | — | — | 33 |

TABLE 7

| Species | Inoculated number | Frequency (kHz) | Voltage (V) | Number of colonies |
|---|---|---|---|---|
| S.cerevisiae | 5,600 | 10 | 10 | 29 |
|  | 5,600 | — | — | 2,093 |

EXAMPLE 2

Figure 2:
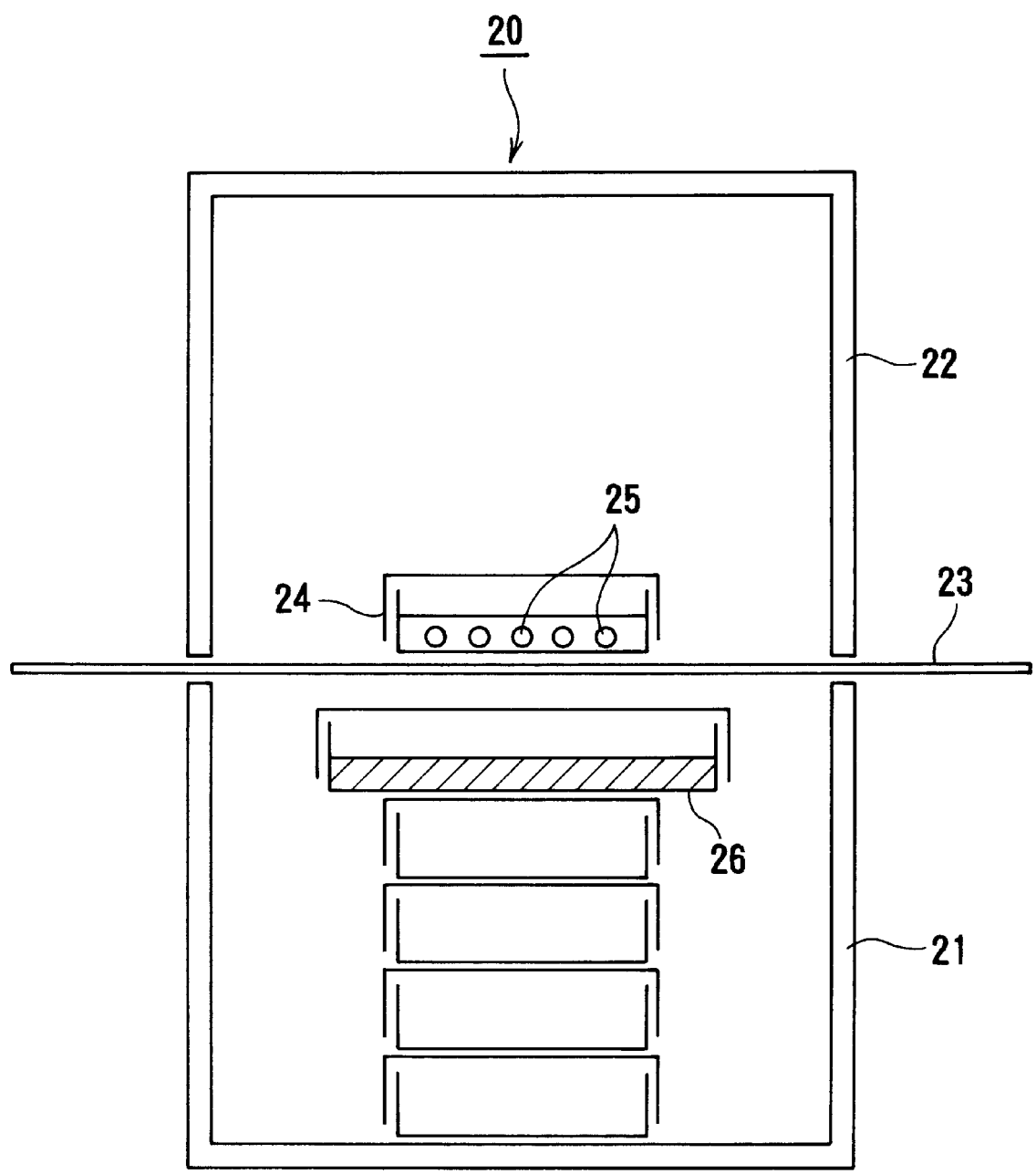
FIG. 2 is a block diagram showing another form of cell culture apparatus in accordance with the present invention.

A cell culture apparatus (20) as shown in FIG. 2 was constructed to hatch medaka eggs.

This culture apparatus (20) consisted of acrylic cylindrical containers (21) (22) of 100 mmh×150 mmφ×3 mmt stacked on each other with a polyvinyl chloride plate (23) therebetween. On the polyvinyl chloride plate (23) there was placed a plastic Petri dish (24), in which medaka eggs (25) were cultured at room temperatures until they were hatched. Directly beneath the polyvinyl chloride dish (23), there was disposed a 9 cm.-dia. plastic Petri dish (25), in which 10" of *Bacillus subtilis* were grown.

Figure 3:
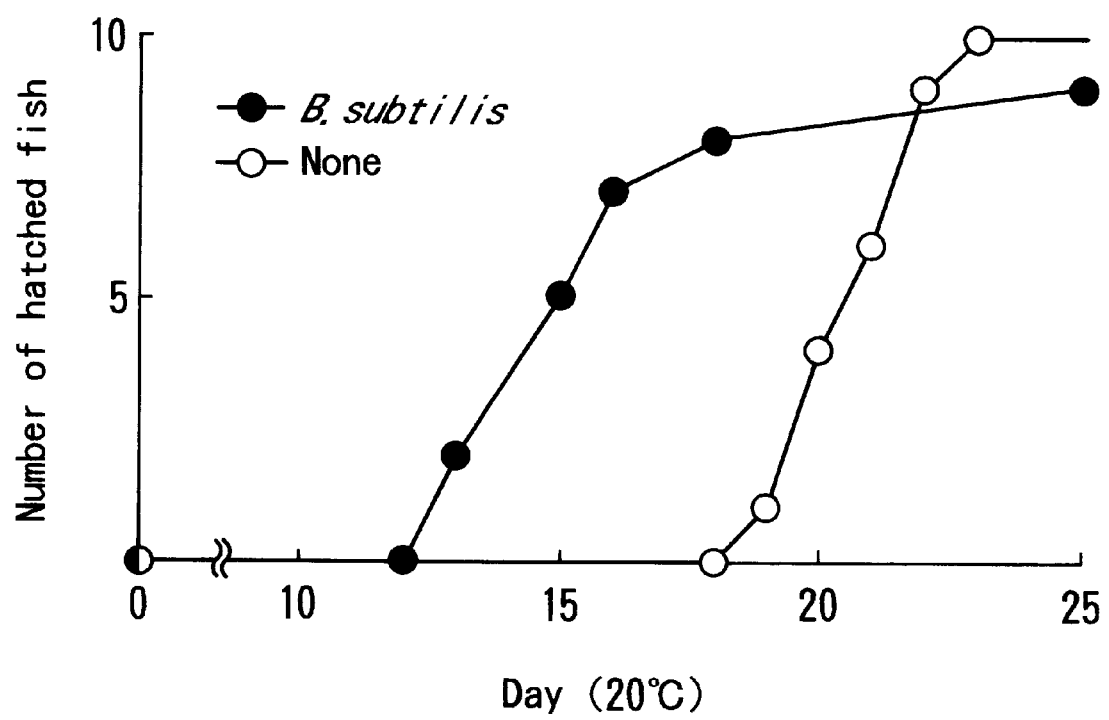
FIG. 3 is the result showing the number of days it takes medaka (*Orizia latipes*) eggs to become hatched, when the apparatus of FIG. 2 is employed.

The result as shown in FIG. 3 demonstrated that in the absence of *Bacillus subtilis*, the medaka eggs began hatching 19 days later, 80 percent of which were hatched after 22 days in culture. Where they were cultured together with the bacteria, they started hatching in 13 days, 80 percent of which were hatched after 18 days in culture.

The above results confirmed that it is possible to accelerate the hatching of medaka eggs by growing them together with *Bacillus subtilis* in the same container, with a polyvinyl chloride plate placed therebetween.

EXAMPLE 3

Figure 4:
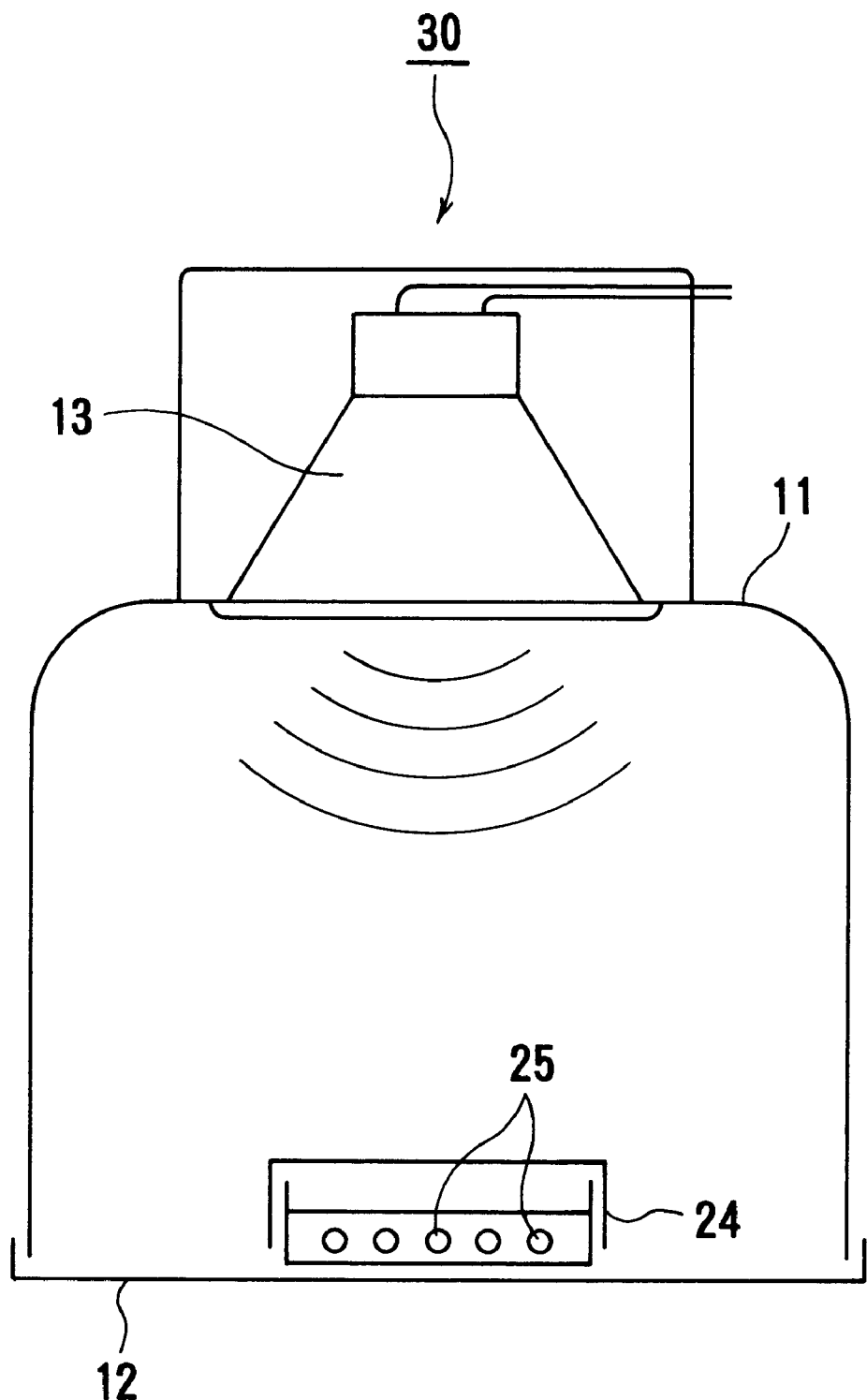
FIG. 4 is a block diagram showing a further form of cell culture apparatus in accordance with the present invention.

A culture apparatus (30) as indicated in FIG. 4 was constructed, and medaka eggs were incubated therein until they were hatched.

A polypropyrene cylindrical container (11) same as in Example 1 was mounted inversely with a polyethylene cover (12) thereof at the bottom. On top of this container (11) a loudspeaker (13) was mounted, and by placing on the polyethylene cover (12) a 6 cm.-dia. plastic Petri dish (24), in which medaka eggs (25) were grown at 24° C. until they were hatched.

Figure 5:
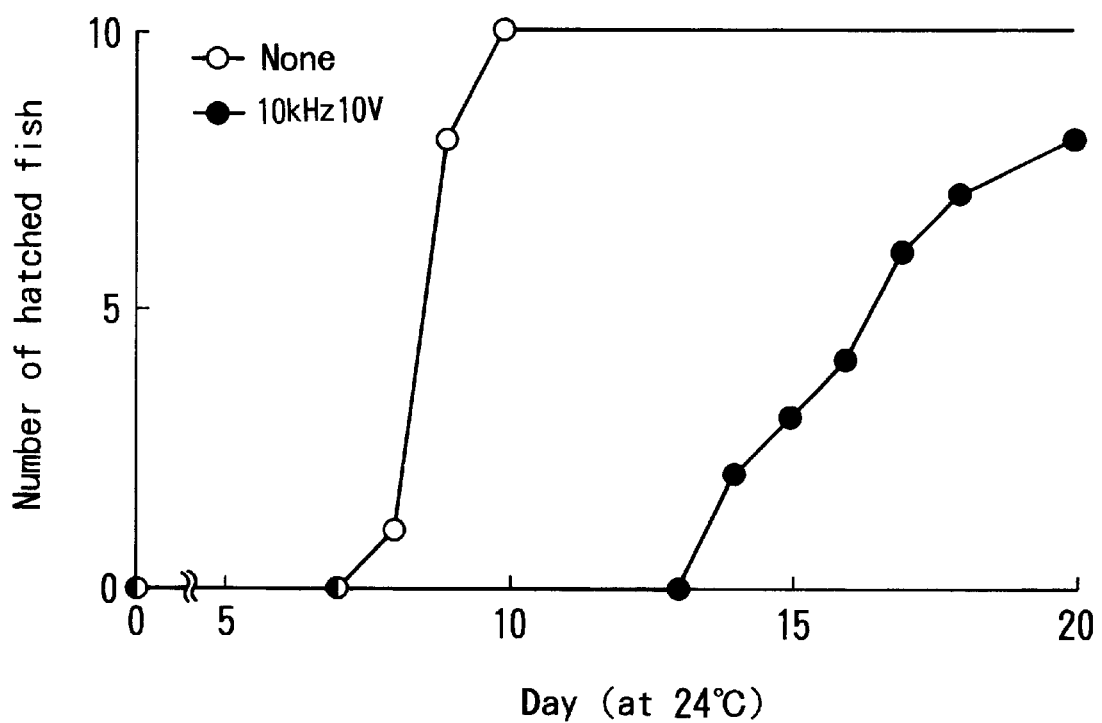
FIG. 5 is the result showing the number of days it takes medaka eggs to become hatched, when the apparatus of FIG. 2 is employed.

The result was illustrated in FIG. 5 which showed that in the absence of sound wave exposure, 80 percent of the medaka eggs hatched in 9 days, while it was not until the 20th day, that they hatched when exposed to a sound wave of 10 kHz with 10 V.

EXAMPLE 4

The same culture apparatus (10) as in Example 1 was placed in a $CO_2$ incubator, where mouse mammary tumor cell FV3A was cultured in ES medium containing serum.

As a result of this culture, the proliferation of FV3A was more markedly repressed when they were exposed with a sound wave of 10 kHz with 10 V than when they were not.

EXAMPLE 5

Figure 6:
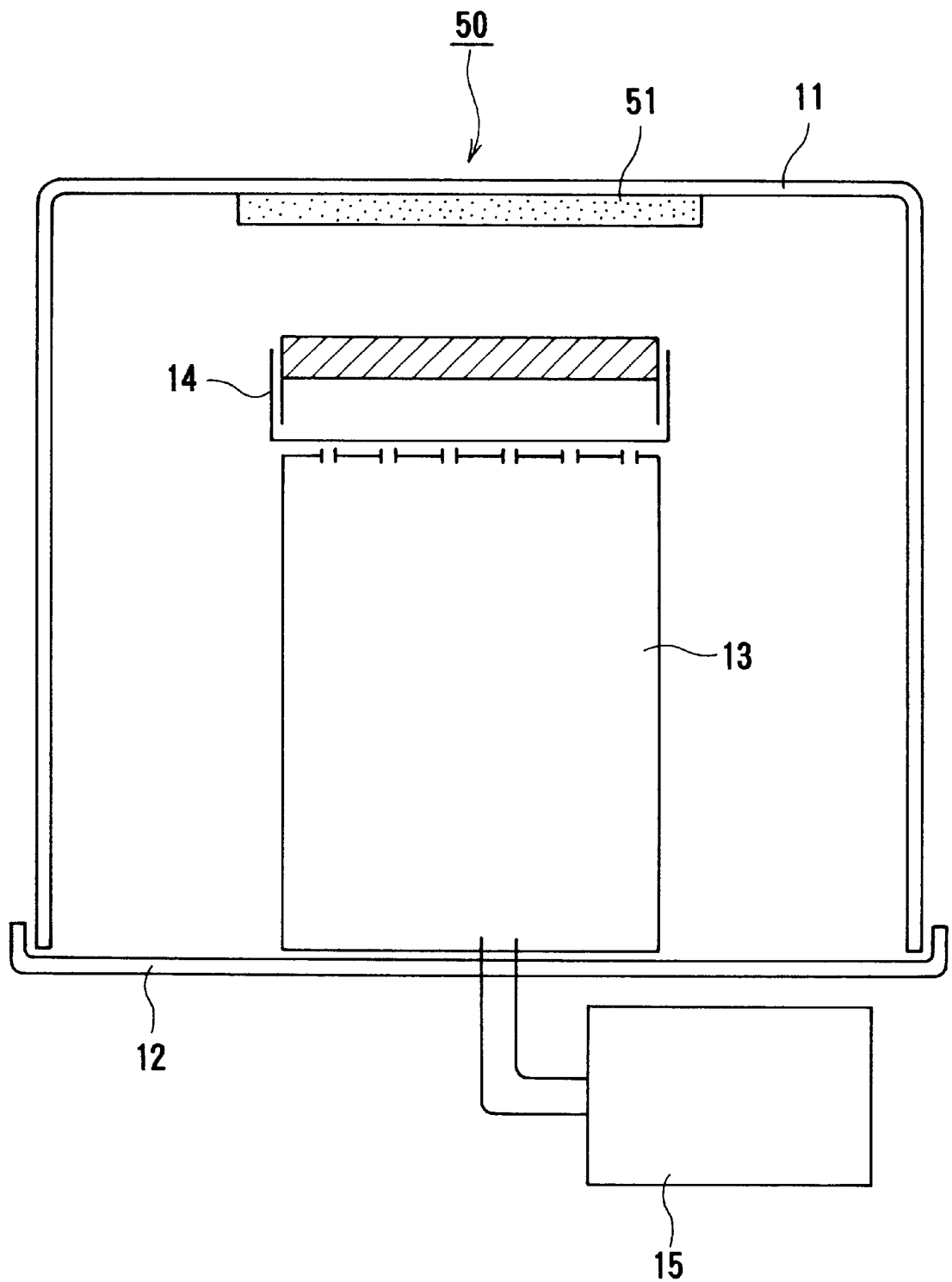
FIG. 6 is a block diagram showing a still further form of cell culture apparatus in accordance with the present invention.

A culture apparatus (50) as indicated in FIG. 6 was construced, and *Bacillus carboniphilus* was cultured under the same conditions as in Table 1.

This culture apparatus (50) was based on the cell culture apparatus (10) as used in Example 1, with graphite (51) disposed in the upper portion thereof The bacteria in a Petri dish (14) considerably accelerated their proliferation in the presence of the sonic signal produced by a speaker (13) and the graphite (51).

When the graphite was encased in a polyethylene bag, a similar effect was observed.

EXAMPLE 6

Using a similar Petri dish (14) as employed in Example 1, *Escherichia coli* was cultured under the same condition as in Table 1. The Petri dish was divided into two portions with a plastic division wall: one portion being *E. coli* cultured and the other containing powdered graphite at a concentration of 1.25 or 6.25 percent. The cells were cultured by exposing thereto the sound waves from a buzzer (Panasonic EB2313, 3VDC).

Figure 7:
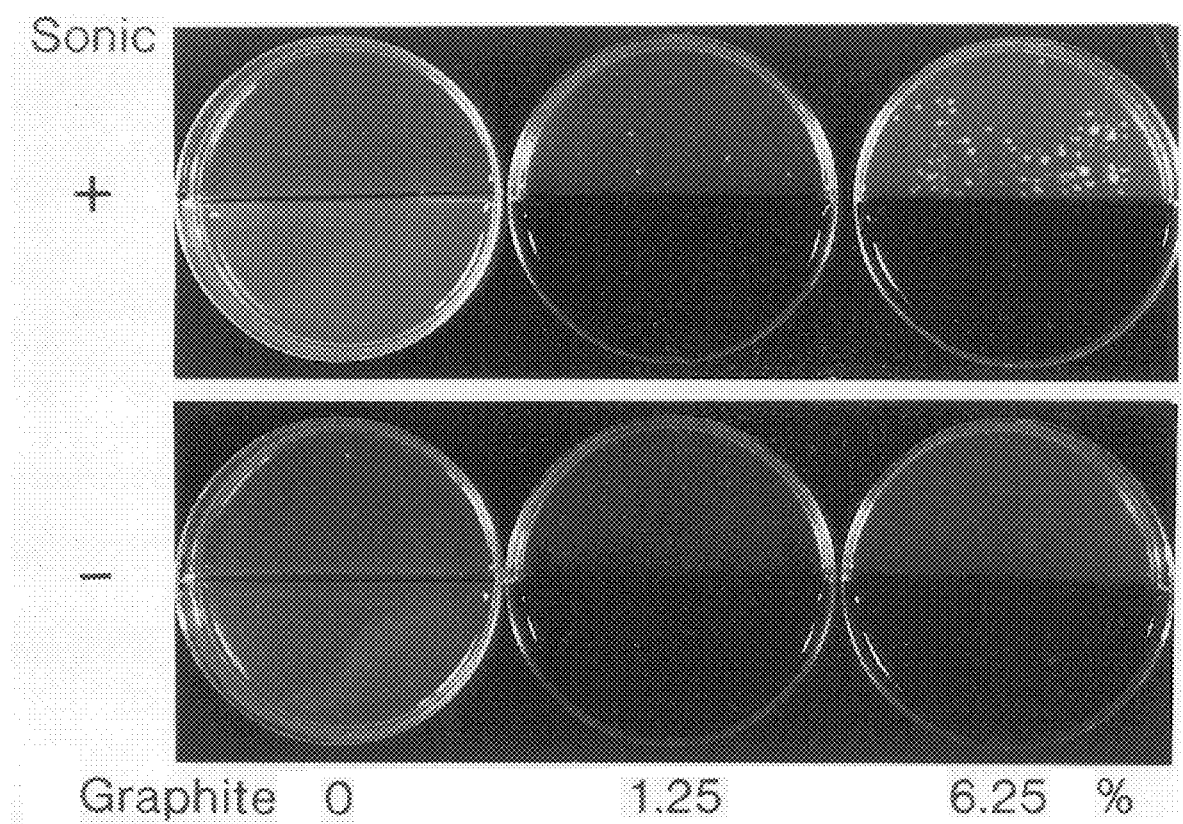
FIG. 7 is a photograph showing the state of growth of *Escherichia coli*.

The result was as indicated in the photograph of FIG. 7. It was only on the portion of the Petri dish containing graphite that the growth of *E. coli* was observed, and the enhancement of growth depended on the amount of graphite used. On the other hand, in the absence of graphite, or in the presence of graphite but no buzzer, no growth of *E. coli* was observed.

EXAMPLE 7

Figure 8:
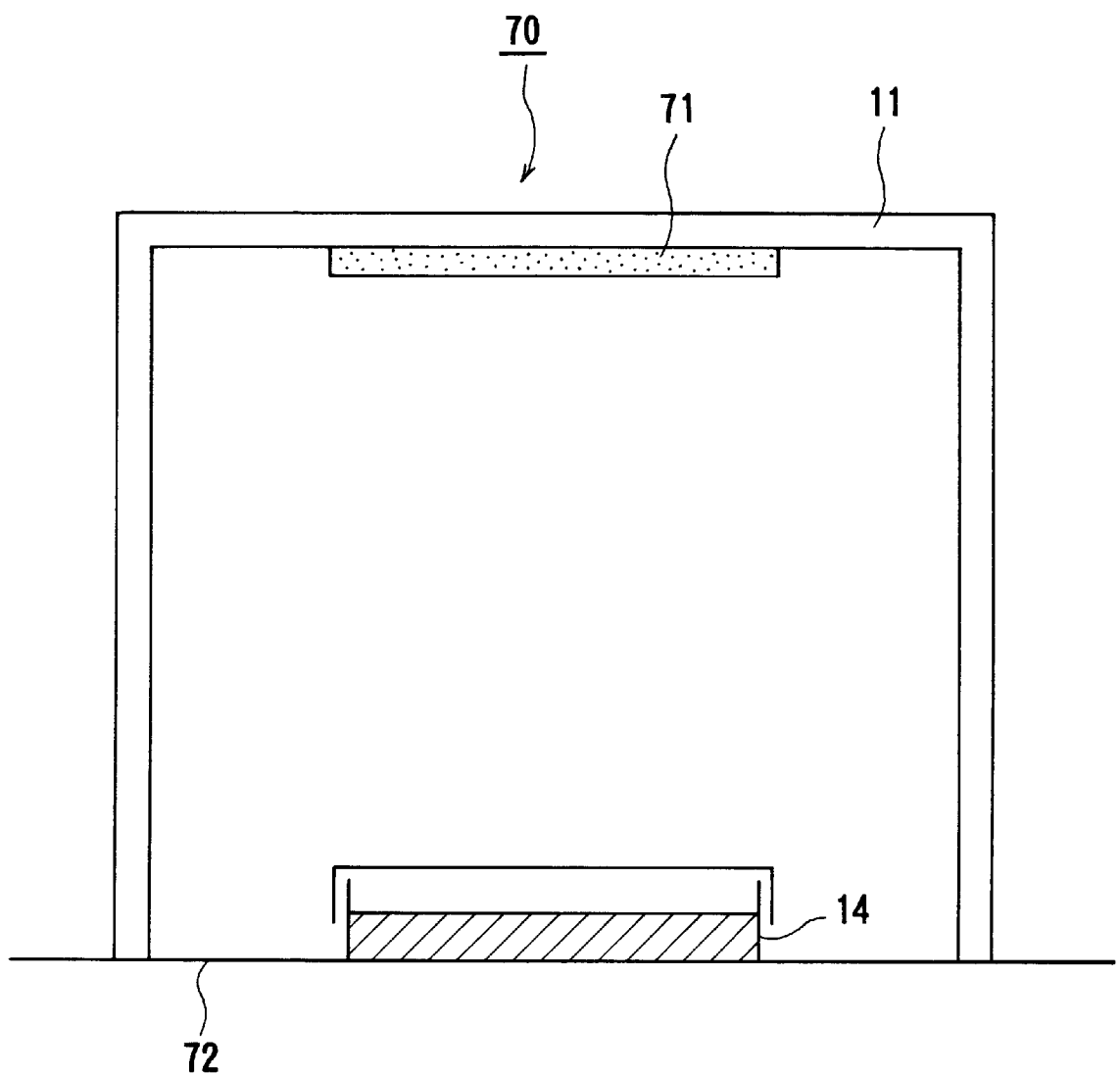
FIG. 8 is a block diagram showing a further form of cell culture apparatus in accordance with the present invention.

A culture apparatus (70) as indicated in FIG. 8 was constructed, and *Bacillus carboniphilius* was cultured under the same conditions as in Table 1.

This culture apparatus (70) was based on the same polypropylene cylindrical container (11) as that used in Example 1. The container (11) stands inversely on a thin film (72) on which a Petri dish (14) being mounted, and adheres cork plates (71) different in thickness on the ceiling, thereby serving as an echo box.

Figure 9:
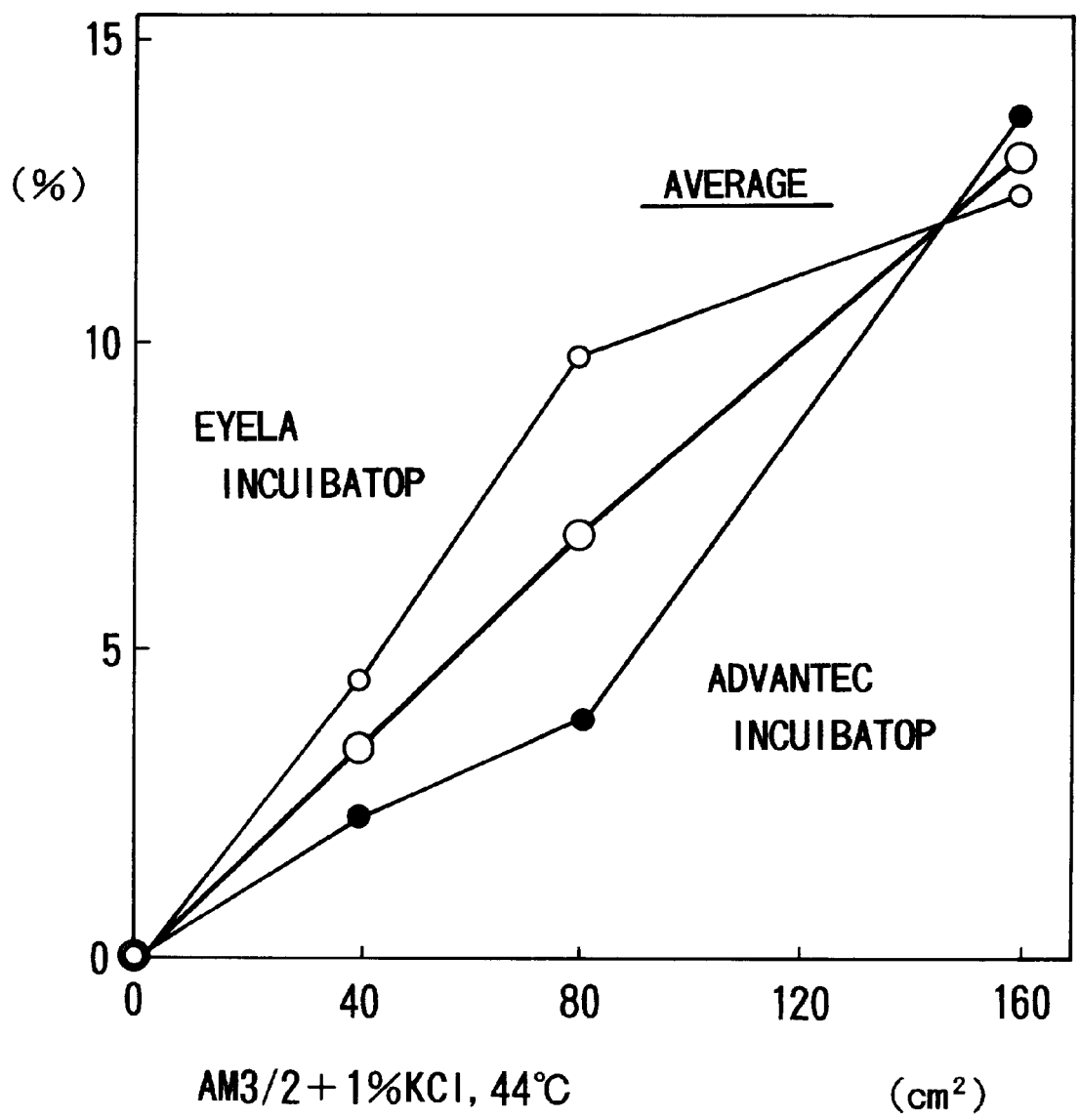
FIG. 9 is a result showing the state in which bacteria were proliferated in the apparatus of FIG. 8.
Figure 10:
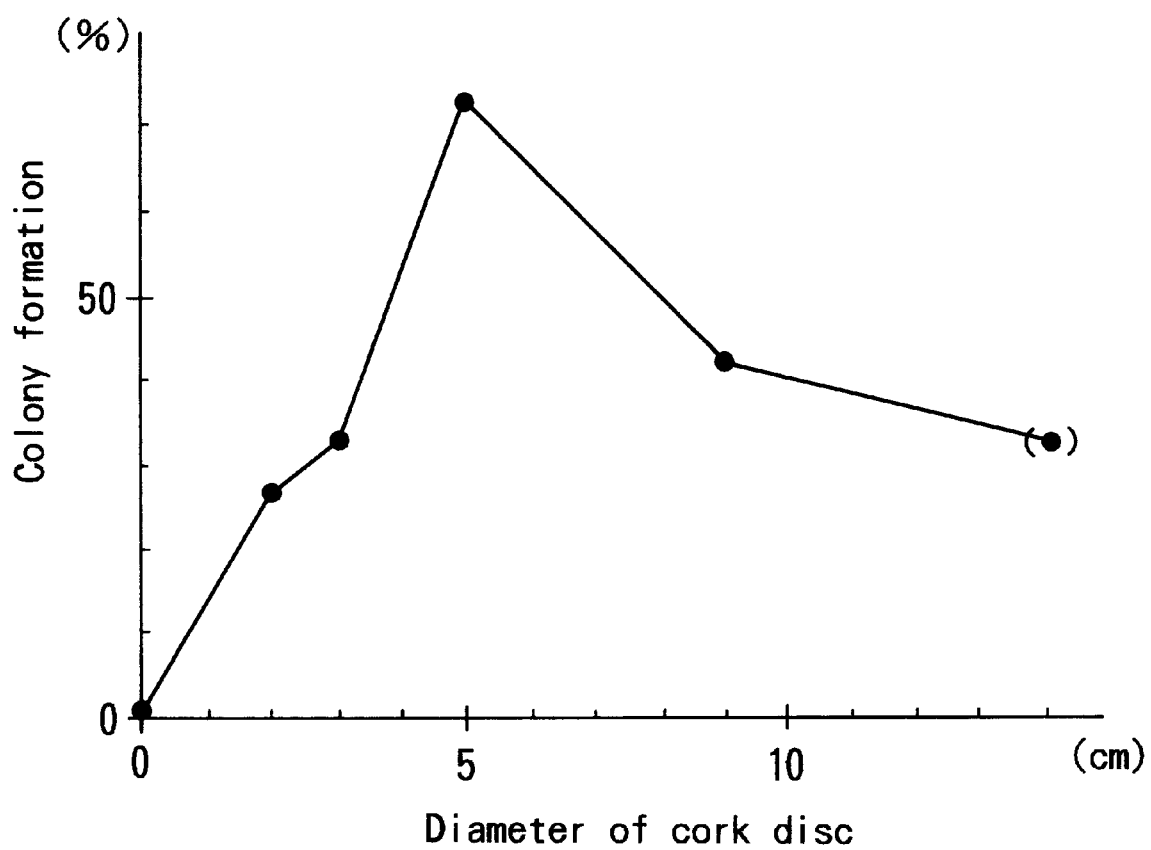
FIG. 10 is another result showing the state in which bacteria were proliferated in the apparatus of FIG. 8.

The results were shown in FIGS. 9 and 10. It was only when a cork plate (71) was present in the echo container that the proliferation of *Bacillus carboniphilus* was observed. However, proliferation varied depending on the thickness of the cork plate (71); it kept being accelerated until a certain thickness was attained, but beyond that, it turned slowing down.

Similar results were obtained when cultures were conducted using other carbon materials (e.g., graphite), synthetic organic polymers or inorganic substances.

EXAMPLE 8

Figure 11:
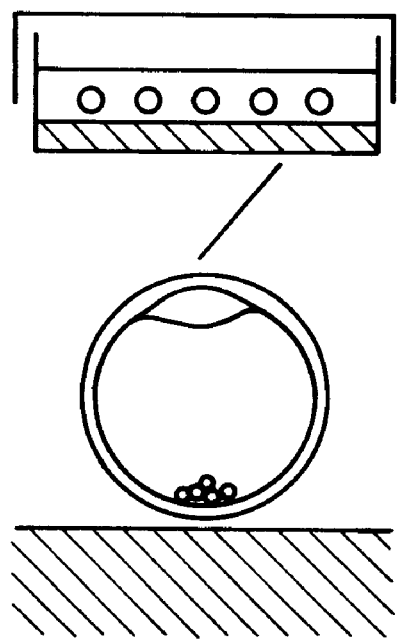
FIG. 11 is block diagram showing the construction of Petri dish for the culture of medaka eggs.
Figure 11:
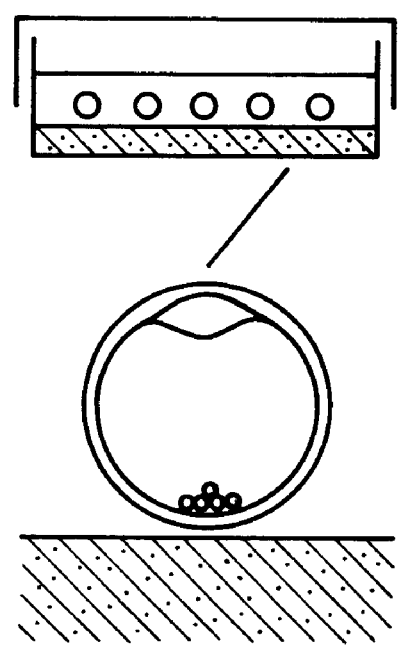

In this example, a culture apparatus (20) was employed, and medaka eggs were hatched therein. This apparatus was essentially the same as that in Example 2, but differed in that 1.5% agar mixed with 2.5% graphite or activated charcoal, as indicated in FIG. 11, lay over the bottom of a Petri dish (24). Another Petri dish in which 1.5% agar was laid was also prepared.

Figure 12:
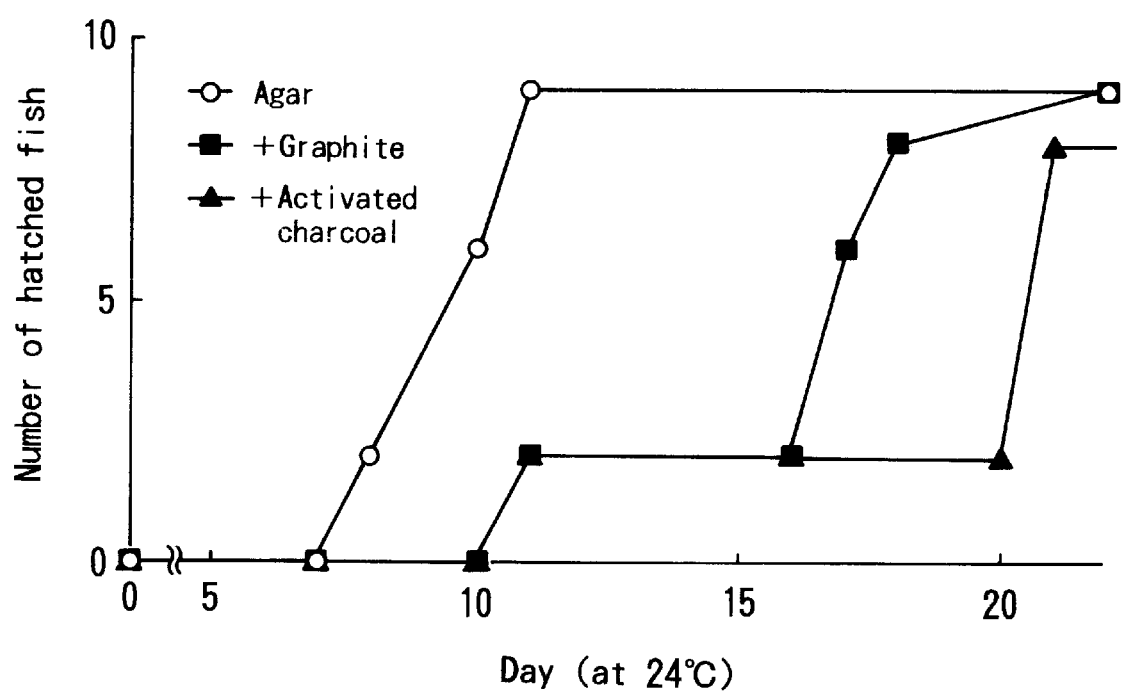
FIG. 12 is the result showing the number of days it takes the medaka eggs to become hatched when the Petri dishes as indicated in FIG. 11 is used.

The result was given in FIG. 12, which showed that the medaka eggs cultured on the agar started hatching 8 days later, and completed hatching after 11 days in culture. It took 18 days for 80 percent of the eggs to hatch in the case of the agar containing graphite, and 21 days in the case of agar containing activated charcoal.

What is claimed is:

1. A process for cell culture, which comprises culturing a microorganism or cells isolated from a multicellular organism while exposing the microorganism or cells to a sound wave of 5–100 kHz derived from a sound producing device.

2. A process for cell culture, which comprises culturing a microorganism or cells isolated from a multicellular organism on a culture plate in a container in which a carbon material, a synthetic organic polymer, or an inorganic substance is present, while exposing the microorganism or cells to a sound wave of 5–100 kHz derived from a sound producing device, wherein the carbon material is selected from the group consisting of graphite, activated carbon, charcoal, cork and plant pith, and the inorganic substance is selected from the group consisting of soil, sea sand and pumice.

\* \* \* \* \*